US008802031B2

(12) United States Patent
Lee et al.

(10) Patent No.: US 8,802,031 B2
(45) Date of Patent: Aug. 12, 2014

(54) LIQUID DISPENSING DEVICE WITH A CAP AND A DIAPHRAGM

(75) Inventors: Martin Alan Lee, Wiltshire (GB); David James Squirrell, Wiltshire (GB); Georgina Martin, Wiltshire (GB)

(73) Assignee: Enigma Diagnostics Limited (GB)

( * ) Notice: Subject to any disclaimer, the term of this patent is extended or adjusted under 35 U.S.C. 154(b) by 149 days.

(21) Appl. No.: 12/065,659

(22) PCT Filed: Sep. 5, 2006

(86) PCT No.: PCT/GB2006/003261
§ 371 (c)(1),
(2), (4) Date: Aug. 7, 2008

(87) PCT Pub. No.: WO2007/028966
PCT Pub. Date: Mar. 15, 2007

(65) Prior Publication Data
US 2008/0314855 A1 Dec. 25, 2008

(30) Foreign Application Priority Data
Sep. 5, 2005 (GB) .................................. 0517910.6

(51) Int. Cl.
*B01L 3/02* (2006.01)
*B01L 3/00* (2006.01)
(52) U.S. Cl.
USPC ........................... 422/521; 422/501; 422/515
(58) Field of Classification Search
CPC .............. G01N 2035/103; G01N 2035/00534;
G01N 35/1079; G01N 35/1002; B01L
2200/025; B01L 2200/141; B01L 2200/16;
B01L 2300/044; B01L 2300/0672; B01L
2300/0867; B01L 9/00; B01L 2400/0481;
B01L 3/021
USPC ........................................... 422/100; 215/228
See application file for complete search history.

(56) References Cited

U.S. PATENT DOCUMENTS

| | | | |
|---|---|---|---|
| 2,781,063 A * | 2/1957 | Williams | 141/24 |
| 4,047,438 A * | 9/1977 | Sekine | 73/863.32 |
| 4,444,062 A | 4/1984 | Bennett et al. | |
| 4,511,534 A | 4/1985 | Bennett, Jr. et al. | |
| 4,537,231 A | 8/1985 | Hasskamp | |
| 4,626,509 A | 12/1986 | Lyman | |
| 4,634,023 A * | 1/1987 | Tanaka et al. | 222/105 |
| 5,118,474 A | 6/1992 | Rogalsky | |
| 2003/0223910 A1 | 12/2003 | Jackson, III et al. | |

(Continued)

FOREIGN PATENT DOCUMENTS

| | | |
|---|---|---|
| EP | 0215536 A2 | 3/1987 |
| EP | 0865824 A1 | 9/1998 |

(Continued)

OTHER PUBLICATIONS

International Search Report for PCT/GB2006/003261 dated Nov. 17, 2006; 3 pages.

(Continued)

*Primary Examiner* — Dean Kwak

(57) ABSTRACT

A liquid dispensing device comprising a hollow body having an opening in a lower end thereof for receiving liquid, and an integrated cap member arranged to sealingly close the body, said cap member comprising a resilient diaphragm which is deformable in a downwards direction. The device is suitable for use in automated apparatus.

6 Claims, 5 Drawing Sheets

(56) References Cited

U.S. PATENT DOCUMENTS

| | | |
|---|---|---|
| 2006/0222570 A1 | 10/2006 | Molitor |
| 2009/0191097 A1* | 7/2009 | Hanafusa et al. ............. 422/100 |
| 2009/0298129 A1* | 12/2009 | Spence et al. ................ 435/91.2 |

FOREIGN PATENT DOCUMENTS

| | | |
|---|---|---|
| EP | 0982073 A2 | 3/2000 |
| EP | 0982072 A3 | 9/2000 |
| EP | 1103305 A1 | 5/2001 |
| EP | 1707269 A2 | 10/2006 |
| JP | 1206260 | 8/1989 |
| JP | 2538844 | 7/1996 |
| WO | 9500392 A1 | 1/1995 |
| WO | 2005019836 A2 | 3/2005 |
| WO | WO 2005019836 A2 * | 3/2005 |

OTHER PUBLICATIONS

Office Action for European Patent Application No. 06779281.2, mailed Dec. 14, 2011, 3 pages.

* cited by examiner

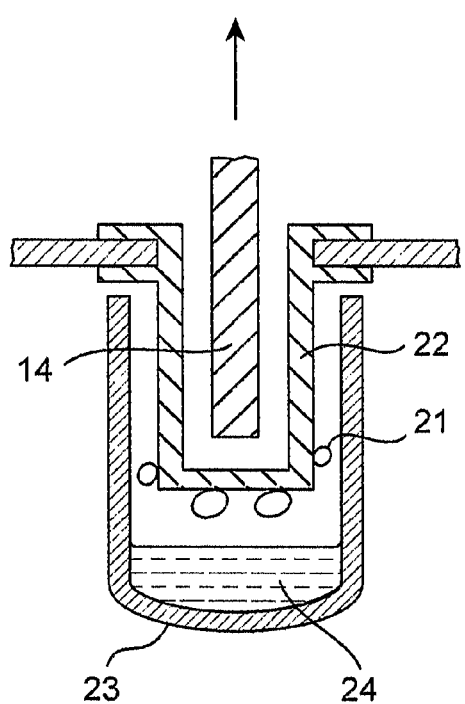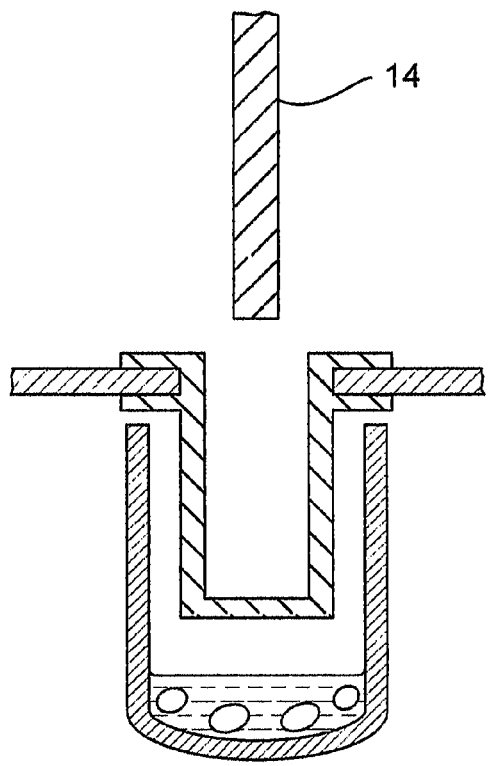
Fig. 6 (contd.)

LIQUID DISPENSING DEVICE WITH A CAP AND A DIAPHRAGM

The present invention relates to a device for moving liquids in particular chemical or biochemical liquid reagents from one vessel to another, as well as apparatus, which incorporates such devices.

The transfer of liquids such as chemical or biochemical reagents using hand held pipettors is well known. Pipettors of this type comprise a hollow body having a conical tip wherein the lower region is open to receive liquids. A bulb of an elastomeric material such as rubber is fitted over the upper end of the body. Squeezing of the bulb in a lateral direction expels air from the device and the resultant suction when the bulb is released whilst the open tip is in the liquid, draws liquid upwards into the body. It can then be moved from one place to another and dispensed by applying further manual pressure to the bulb.

These simple devices are effective, but it can be difficult to ensure that accurate volumes of liquid, in particular where these are small, are dispensed.

Furthermore, such devices are not suitable for use in robotic workstations and other automated biochemical systems, where accuracy of measurement is required and where it is necessary to transfer materials without manual intervention.

Such robotic workstations and automated biochemical systems are now in widespread use for a variety of research and diagnostic purposes. Quantities of liquids are transferred automatically into or out of reaction vessels or wells in order to allow for the enormous range of chemical, biochemical and biological reactions currently in use to be carried out. In many instances, these simultaneously transfer multiple liquid samples, and 96 or even 348 reaction wells may be filled simultaneously.

In order to draw liquid into the pipettor tip, these workstations and systems may use vacuum pumps which are attached via tubing to the upper ends of the pipettor tips. Alternatively, they may use pistons to positively draw liquid up into the pipettor tip.

Such devices can be cumbersome. Furthermore, it is possible that aerosol contamination may enter the pipettor tip through the open upper end. In order to prevent this, filters are frequently provided within the body of the pipettor. Such filters are not vapour barriers however and where liquids transported in these devices are corrosive, such as bleaching reagents and acids, they may corrode the pipettor.

The present invention provides an improved liquid dispensing device. The liquid dispensing device (which may alternatively be called a liquid transfer device) can be used to move or transfer quantities of liquids from one vessel or area to another.

According to the present invention, there is provided a liquid dispensing device comprising a hollow body having an opening in a lower end thereof for receiving liquid, and an integrated cap member arranged to sealingly close the body, said cap member comprising a resilient diaphragm which is deformable in a downwards direction.

As used herein, the expression "integrated" used in relation to the cap member means that the cap member and the hollow body to which it is associated form a coherent unit. Although the cap member may be removable from the hollow body, it is not attached to any other elements associated with apparatus. In particular, the device may take the form of a two-part assembly of an individual hollow body associated with an individual cap member which forms a self-supporting discrete unit.

However, in some cases, it may be useful to combine together devices in the sense that a plurality of bodies may be structurally linked or combined together for example in an array. However, in such cases, each individual body will generally be associated with its own discrete cap member.

In a preferred embodiment the diaphragm is arranged to sealingly close an upper end region of the body in an airtight manner. However, the precise position of the diaphragm may vary depending upon the size of the body, the purpose to which it is to be put, and the materials from which it is constructed.

In a preferred embodiment the cap member is associated with the upper end of the body to form a diaphragm over its upper end. Ideally, the diaphragm extends annularly of the upper end of the body so that it rests or is fixed to an upper surface of the body. Alternatively the diaphragm may be located inside the body, preferably in its upper end region.

Preferably the diaphragm comprises a sheet of resilient material.

Ideally the diaphragm of the cap member is arranged such that it is substantially perpendicular to the longitudinal axis of the body. However the diaphragm may alternatively have a concave profile.

In use, the deformation of the diaphragm in particular by the application of a displacement force downwards onto it, expels air from within the body. The lower region of the body with the opening forms a pipettor tip. When the pipettor tip is immersed in liquid, the displacement force on the resilient diaphragm is released whereupon it returns to its original conformation, and in doing so, draws liquid into the body. The volume drawn in will be directly related to the degree of deformation applied.

The diaphragm is ideally made of an elastomeric material such as a polymer or rubber material. Particular examples of such materials include silicone rubber, natural rubber, nitrile rubber, EPDM or polyurethane. In particular the elasticity of the material as measured by the SHORE rating, is in the range of from 30 A to 120 A, and preferably in the range of from 40 A to 100 A.

The elasticity of the diaphragm will also be affected by the thickness of the material, and typically, this will be in the range of from 0.1-3 mm for pipettors dispensing from 1 microliter to 5 milliliters, for instance from 0.5 to 1 mm for the pipetting of 25 microliters.

The diameter of the cap member is dependent on the size of the body. However, in order to seal most conventional pipettors, in particular those used in automatic device such as those mentioned above, the diameter of the cap member will suitably in the range of from 0.5 to 4.0 cm.

In use, the pressure may be applied to the diaphragm manually or automatically for example using an actuator device. In the latter case, the amount of displacement applied can be accurately controlled to ensure that precise and accurate quantities of liquids are drawn into the body. The fact that the diaphragm is operable using a downwards pressure means that the device is readily useable in automated devices. Thus apparatus including the device as described above, and an actuator which is operable automatically form a further aspect of the invention.

In a further particular embodiment, the diaphragm is provided with an upwardly projecting protuberance, which is generally in the central region of the diaphragm and acts as a "push button" to ensure that the displacement force is applied at the correct position to ensure the appropriate deformation of the upper wall.

The presence of the integrated cap member effectively isolates the contents of the body from the actuator device and therefore the risk of contamination from the area of this device, and in particular cross contamination from aerosol sources, is eliminated. It also allows the pipetting of corrosive liquids without harmful effects being felt in the rest of the device.

In a preferred embodiment the cap member further comprises a sidewall which engages with the body.

Therefore the present invention also provides a liquid dispensing device comprising a hollow body having an opening in a lower end thereof, and a cap member arranged to sealingly close an upper end of the body, said cap member comprising a side wall which engages with said body, and a resilient upper wall, preferably a diaphragm which is deformable in a downwards direction.

In a preferred embodiment the diaphragm is structurally distinct from the side wall and may be substantially perpendicular to the side wall. The side wall generally projects downwardly from the diaphragm and engages either the internal or external surface of the body. Preferably, the side wall is of a resilient material, in particular a similar resilient material to that of the diaphragm.

In a particular embodiment, the side wall engages with an internal surface of the body. In this case, the diaphragm suitably extends annularly of the side wall so that in use, it rests on the upper surface of the body. The cap member may be fixed to the body or alternatively may be removable.

In a particular embodiment, the diaphragm is integral with the side walls, so that they may be produced for example in a single moulding operation.

If desired, the side walls may be thicker to ensure that the resilience is lower, so that good contact with the internal walls of the pipettor body can be ensured and maintained.

The cap member is suitably generally round in transverse section, to fit into a conventional round pipettor body.

In a further preferred embodiment, one or more annular rings are provided around the outer surface of the side walls, which are arranged to ensure that an effective seal is formed between the internal walls of the pipettor body and the cap member.

Cap members for use in the liquid dispensing device form a further aspect of the invention.

The hollow body of the device is suitably of a rigid material such as a rigid plastics material, which is optionally transparent. Particular examples of such materials include glass or plastics such as polypropylene, polyethylene, polystyrene or polyamides. The entire body may be generally conical in shape, but preferably, an upper region is generally tubular, so that it can readily accommodate side walls of the cap member. Alternatively a region of the body, preferably a lower region may comprise a capillary tube. The upper and lower regions may be integral with each other and made of the same material, or they may be of different materials which are fused or clipped together.

The liquid dispensing device is suitably disposable.

The body may carry external features which enable it to be located and manipulated within an automated device such as those described above. These features may include flanges or ridges which act as location or fixing devices within the apparatus, so as to allow the actuator to impact on the diaphragm to conduct a liquid aspiration operation automatically. Alternatively, they may be adapted to interact with moving arms or the like, to facilitate the automatic movement of the liquid dispensing device from one part of an apparatus to another.

In a further aspect, therefore, the invention provides apparatus for conducting a chemical or biochemical reaction, said apparatus comprising a liquid dispensing device as described above and an actuator which is moveable automatically so as to deform the diaphragm of the liquid dispensing device in a downwards direction.

The apparatus suitably further comprises means for locating said liquid dispensing device in a predetermined position within the apparatus so that the actuator can operate thereon.

Suitably the actuator is a rod, moveable in the direction of the pipettor tip, but any convenient mechanical plunger may be utilised such as a cam.

In a particularly preferred embodiment the actuator is a magnetic rod.

In such cases, the apparatus can be readily modified to carry out multiple functions such as the transfer of magnetic particles such as superparamagnetic beads used in immunoseparation. It is necessary only to replace the liquid dispensing device with a sheath, for example using the locating means to allow sequential operations to aspirate and/or dispense liquid or move magnetic beads.

Such devices and their use in moving magnetic beads or the like from one reaction vessel to another are well known in the art. When the magnet is located within the sheath, magnetic beads in the vicinity of the sheath are attracted to it and so these can be moved from one vessel to another. Removal of the magnet from the sheath when is located in the vessel in where the beads are required means that the beads are automatically dispensed. Such arrangements are used both in hand held devices such as the Bio-nobile PickPen® and in apparatus such as the Kingfisher® apparatus from Thermo-Labsystems.

A particular example where such a process may be useful is illustrated hereinafter.

Movement of the actuator is suitably effected using a motor such as a worm drive, which is arranged to move the actuator along the axis of the pipette tip. The motor is suitably controlled by a microprocessor or the like, to ensure that accurate movement, and thus accurate volumes of liquid are aspirated or dispensed.

In a particular embodiment, the microprocessor is provided with a temperature sensor that, through the microprocessor, can be used calibrate out effects of temperature, which might otherwise affect the accuracy of the system.

Particularly suitable apparatus that may be modified to incorporate the liquid dispensing device of the present invention is described in WO2005019836, the subject matter of which is hereby incorporated by reference. In that device, a magnetic rod, useful in the automatic transfer of magnetic beads, provides a suitable actuator for the liquid dispensing device described above.

Whilst single liquid dispensing devices may be utilised, more than one such device may be used in together, for example to allow for the simultaneous automatic filling of multiple wells or reaction vessels. For example conventional 48, 96 or 384 well plates, such as those used in high-throughput screening applications, can be filled using liquid dispensing devices as described above.

The use of the device and apparatus as described above to transfer liquids forms a further aspect of the invention.

Thus the invention further provides a method of moving a liquid reagent from one vessel to another, which method comprises aspirating said liquid into a liquid dispensing device as described above by depressing the diaphragm of the cap member, releasing pressure from said cap member whilst the open end of the body is immersed in said liquid reagent so as to aspirate the liquid into the body, moving the vessel or the device so that the device is aligned with a different vessel, and dispensing the liquid by depressing the diaphragm of the cap member of the device.

The method is suitably conducted automatically, in particular in apparatus as described above.

In particular circumstances, this process may be combined with the transfer of magnetic beads, using a modified form of the apparatus as described above, for example to extract and concentrate an analyte from a sample.

In summary, the device of the invention provides for automated fluid transfer, which is both precise and accurate. The actuation mechanism used is completely isolated from the pipetted fluid so as to completely eliminate problems of cross-contamination.

The invention will now be particularly described by way of example with reference to the accompanying drawings in which.

Example 1

Transfer of Liquid

Figure 1:
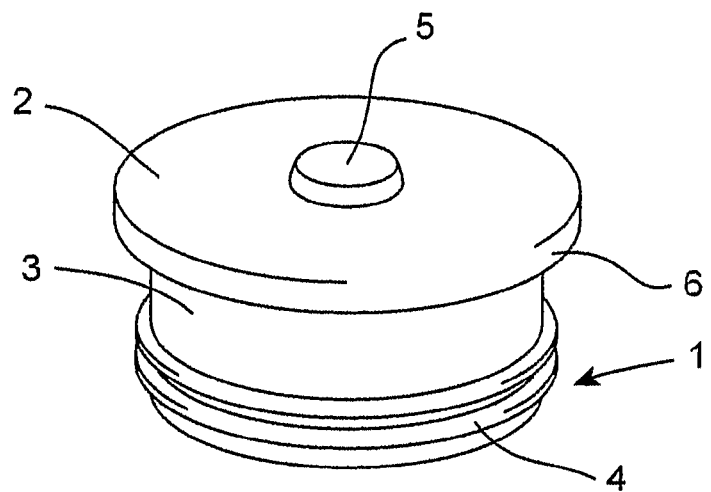
FIG. 1 is a perspective view of a cap member used in an embodiment of the invention.

A range of cap members having the shape of that shown in FIG. 1 were prepared in a range of materials, each having a different elasticity or SHORE rating and thickness.

Each cap member (1) comprised a elastomeric diaphragm (2) integral with a circular supporting side wall (3). The diaphragm extended annularly of the side wall (3) to provide a rim (6).

Annular silicone ridges (4) were provided around the lower regions of the side wall (3), and a protuberance (5) projected upwards from the centre of the diaphragm (2).

Figure 2:
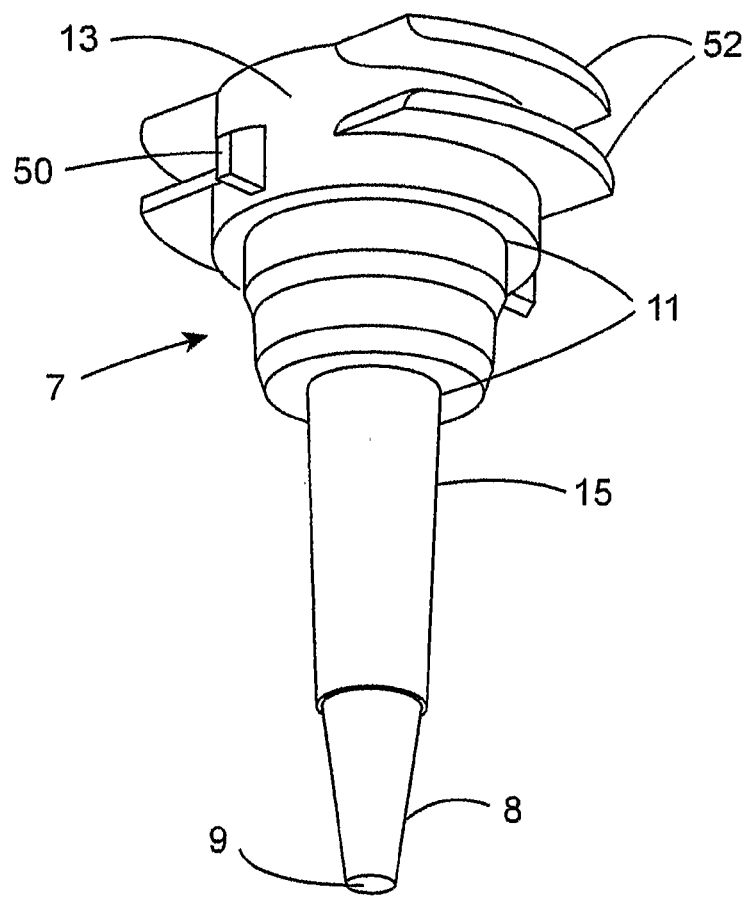
FIG. 2 is a perspective view of a body which may be used in an embodiment of the invention.
Figure 3:
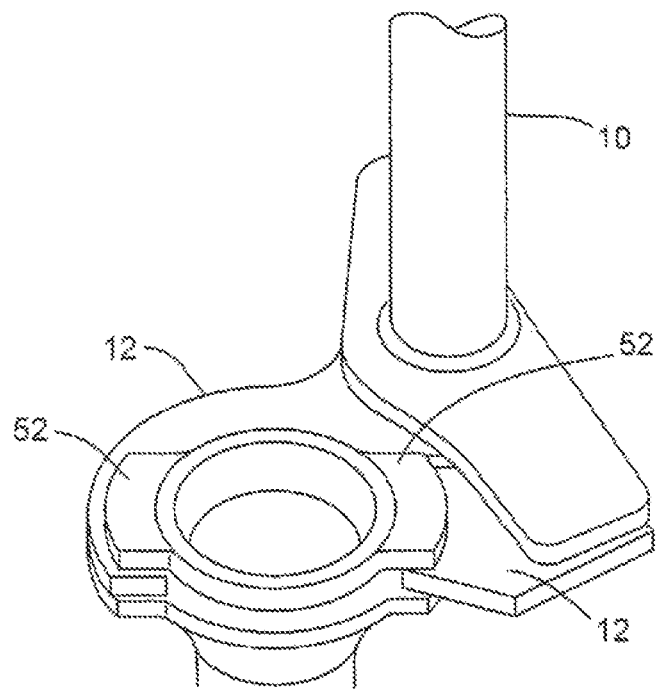
FIG. 3 illustrates how the body of a device of the invention can be arranged in apparatus for automatic processing of reagents.

The cap members were moulded to fit into the opening of a pipettor body (7) illustrated in FIG. 2. This body (7) was made of a rigid plastics material and comprised a lower conical region (8) which terminated in an opening (9), forming a pipettor tip. An upper region (13) was generally cylindrical in internal cross section, and was provided with a series of annular ridges (11) as well as two pairs of opposed flanges (52) which were designed so that the body (7) could be held and manipulated within the device described in WO2005019836 using a fork 12 provided on a moveable arm (10) (FIG. 3). Anti-rotation lugs 50 were also provided and projected from the upper region (13).

In this case, an elongate central cylindrical section (15) was provided between the upper and lower regions (13, 8) so as to allow the pipettor tip to extend into a liquid sample.

Figure 4:
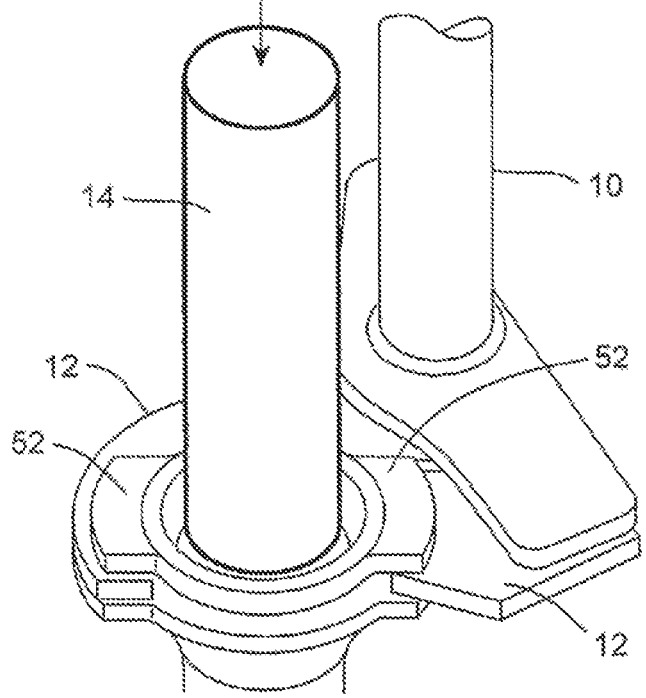
FIG. 4 illustrates how an actuator may interact with the device in the apparatus as illustrated in FIG. 3.

With the cap member (1) in place in a pipettor body (7), the device was introduced into a chamber of the apparatus described in WO2005019836. The device was arranged so that the protuberance (5) was located directly below a vertically moveable magnetic rod (14) provided adjacent the arm (10) and directly above the fork (12) of the device of WO2005019836 (FIG. 4).

Figure 5:
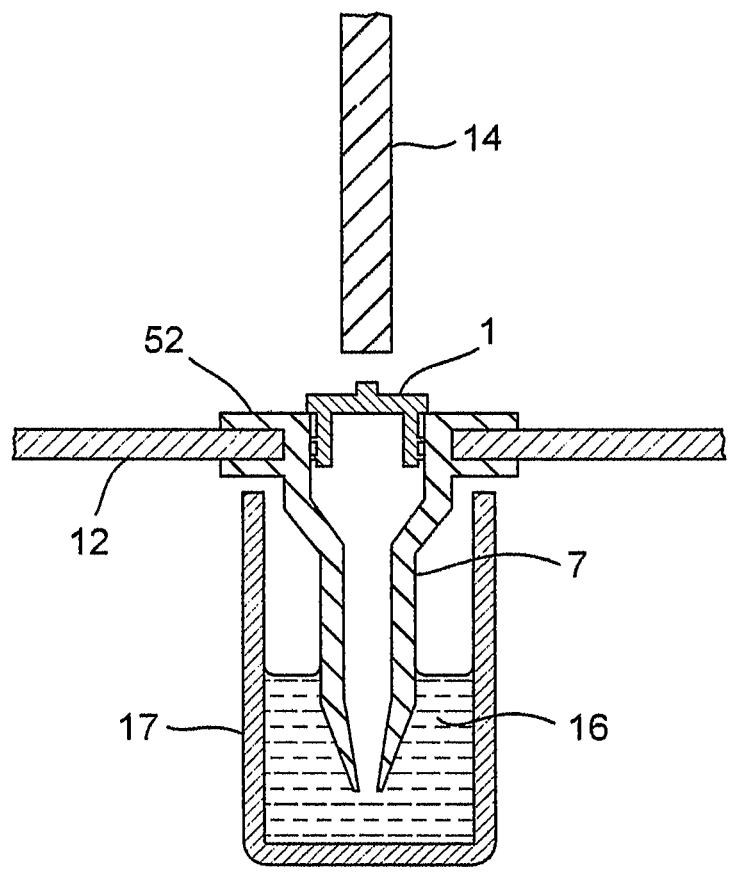
FIG. 5 is a section through a liquid dispensing device of the invention.

The pipettor tip was arranged so that the opening (9) was immersed in a liquid (16) in a reaction vessel (17) and the magnetic rod (14) was lowered (FIG. 5) so as to compress the diaphragm (2) and then raised to release it.

The upwards and downwards movement of the rod was controlled so as to depress and release the diaphragm (2) so as to aspirate a small predetermined volume of liquid into the body 7. The body 7 was then removed from the vessel (17) and the liquid was then dispensed into a measuring vessel positioned under the tip The results are set out in Table 1.

TABLE 1

| Elasticity | Dispensed Volume Thickness (mm) | | |
|---|---|---|---|
| (SHORE rating) | 0.50 | 0.75 | 1.00 |
| 42A | 27.4 ± 0.64 μl (2.3%) | 26.1 ± 0.39 μl (1.5%) | 29.3 ± 0.36 μl (1.2%) |
| 65A | 23.4 ± 0.17 μl (0.7%) | 25.4 ± 0.04 μl (0.2%) | 24.9 ± 0.15 μl (0.6%) |
| 90A | 15.7 ± 0.29 μl (1.8%) | 13.4 ± 0.22 μl (1.7%) | 10.4 ± 0.19 μl (1.9%) |

Values shown are mean ±1 SEM, n = 5 with CV in brackets

These results show that precise and accurate volumes of liquid can be aspirated and dispensed automatically using the device of the invention.

Example 2

Extraction and Concentration of Dissolved or Particulate Materials from Liquid

Figure 6:
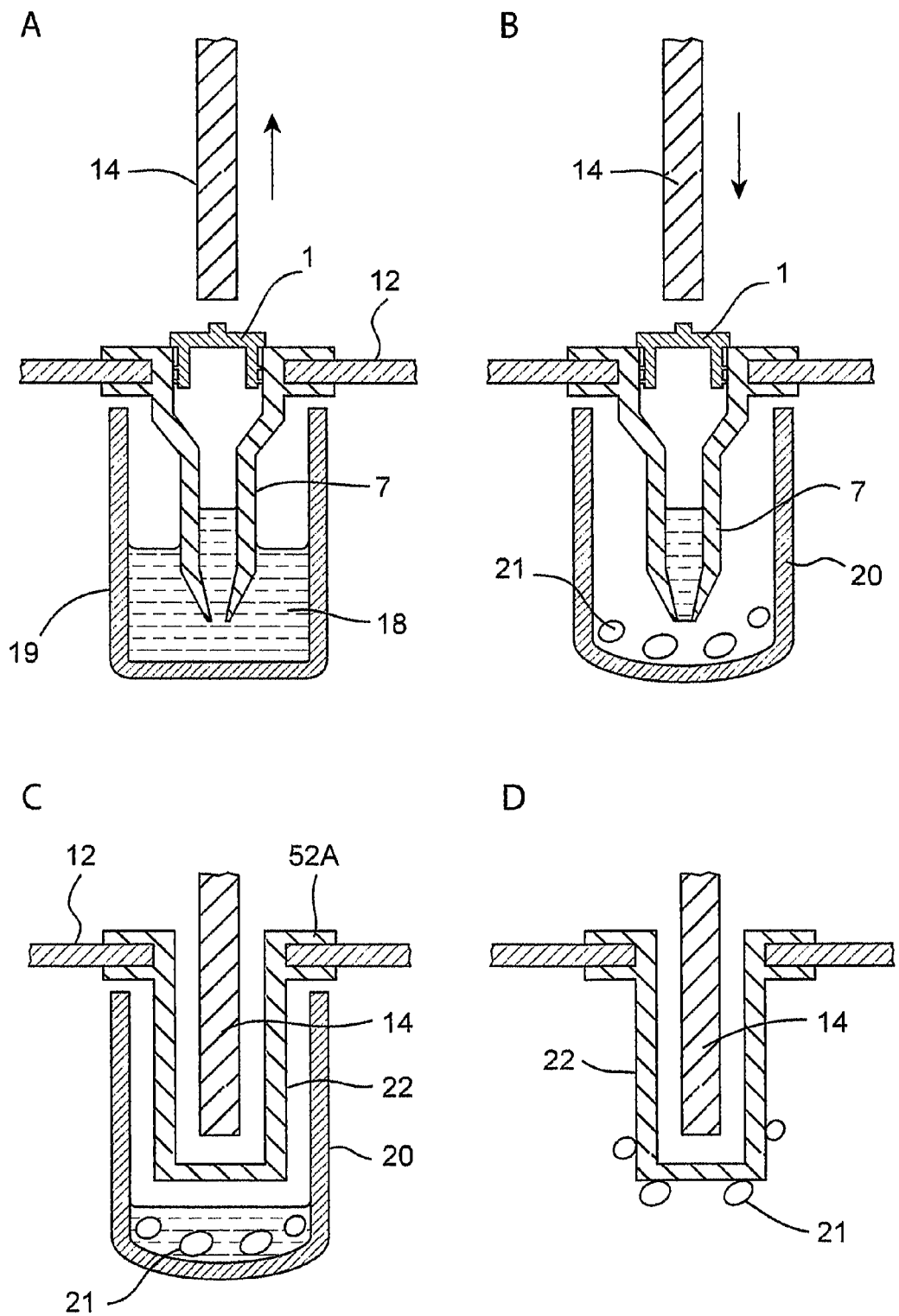
FIG. 6 illustrates schematically a procedure for the extracting and concentrating an analyte from a sample using an embodiment of the present invention.

The apparatus of the invention may be particularly suitable for the extraction and concentration of dissolved or particulate materials from liquid samples using magnetic beads where aspiration and dispensing operations are conducted sequentially with magnetic bead transfer. Such a procedure is illustrated schematically in FIG. 6.

Using the liquid dispensing device of the invention, a sample liquid (18) from a vessel (19) is aspirated into the body (7) of a liquid dispensing device by the sequential downwards and upwards movement of the magnetic rod (14) (A).

The device is then removed from the vessel (18) and aligned with a new vessel (20) which may contain magnetic beads (21), carrying for example, binding agents such as antibodies which are specific for particular target moieties which are found or suspected of being present within the sample (18) (B). Downward pressure on the cap member (1) by the rod at this point will dispense the contents of the body into the vessel (20) to form a mixture of sample and beads.

If preferred however, the liquid may be dispensed first and the beads (21) added subsequently.

The mixture of beads (21) and liquid (18) are incubated together for a sufficient period to allow target moiety within the sample to adhere to the beads (21).

In order to remove the beads (21) from the vessel (20), the liquid dispensing device is replaced with a plastics sheath (22) which is hollow so as to accommodate the magnetic rod (14) therein. The sheath (22) may be provided with similar flanges (52A) to the liquid dispensing device so that is may be accommodated on the fork (12) of the same apparatus (C).

The rod (14) is then lowered into the sheath (22) and the sheath (22) lowered into the region of the beads (21). The beads (21) are attracted to the magnetic rod (14) and therefore will adhere to the external surface of the sheath (22). Removal of the sheath (22) with the rod (14) in position within it will extract the beads (21) from the liquid (18). They can then be taken out of the vessel (20) (D).

In order to dispense the beads (21) into a new vessel (23) which optionally contains wash liquid (24) or the like, the sheath (22) with the rod (14) in position within it and the beads (21) adhered to the external surface is positioned over the vessel (23) (E).

The rod (14) is then withdrawn (F) and then the sheath (22) with adherent beads is lowered into the liquid (24) whereupon the beads (21) are released into the liquid (24).

This procedure is amendable to automation using conventional methods, and in particular using the apparatus of WO2005/019836.

The invention claimed is:

1. A liquid dispensing device consisting of a hollow body (7) and a cap member (1), wherein:
   the hollow body (7) has an opening (9) in a lower end thereof for receiving liquid and an upper opening; and
   the cap member (1) is arranged to sealingly close the upper opening in the body (7), said cap member (1) comprising:
      a resilient planar diaphragm (2) situated substantially perpendicular to a longitudinal axis of the body (7) which is deformable in a downwards direction;
      a resilient side wall (3) which extends downwardly from the diaphragm (2) and engages either an internal or external surface of the body (7); and
      a discrete protuberance (5) projecting upwards from a central region of the diaphragm (2), wherein the discrete protuberance (5) is arranged to receive an applied displacement force;
   wherein the diaphragm (2) has an elasticity corresponding to a SHORE rating from 30 A to 120 A.

2. The liquid dispensing device according to claim 1, wherein the diaphragm (2) comprises a sheet of resilient material.

3. The liquid dispensing device according to claim 1, wherein the diaphragm (2) of the cap member (1) has a thickness from 0.1 mm to 3.0 mm.

4. The liquid dispensing device according to claim 1, wherein the side wall (3) engages the internal surface of the body (7), and wherein the diaphragm (2) extends annularly from the side wall (3) and the diaphragm (2) rests on the upper surface (13) of the body (7).

5. The liquid dispensing device according to claim 1, wherein one or more annular ridges (4) are provided around the outer surface of the side wall (3) of the cap member (1).

6. The liquid dispensing device according to claim 1, wherein the liquid dispensing device is disposable.

* * * * *